(12) United States Patent
Salmon et al.

(10) Patent No.: US 10,874,819 B2
(45) Date of Patent: Dec. 29, 2020

(54) HUMIDIFICATION SYSTEM

(71) Applicant: Fisher & Paykel Healthcare Limited, Auckland (NZ)

(72) Inventors: Andrew Paul Maxwell Salmon, Auckland (NZ); Guohua Bao, Auckland (NZ); Nordyn Alami, Auckland (NZ)

(73) Assignee: Fisher & Paykel Healthcare Limited, Auckland (NZ)

( * ) Notice: Subject to any disclaimer, the term of this patent is extended or adjusted under 35 U.S.C. 154(b) by 780 days.

(21) Appl. No.: 15/125,553

(22) PCT Filed: Mar. 13, 2015

(86) PCT No.: PCT/IB2015/051830
§ 371 (c)(1),
(2) Date: Sep. 12, 2016

(87) PCT Pub. No.: WO2015/136489
PCT Pub. Date: Sep. 17, 2015

(65) Prior Publication Data
US 2017/0007798 A1    Jan. 12, 2017

Related U.S. Application Data

(60) Provisional application No. 61/953,571, filed on Mar. 14, 2014.

(51) Int. Cl.
*A61M 16/16* (2006.01)
*A61M 16/10* (2006.01)
(Continued)

(52) U.S. Cl.
CPC ........ *A61M 16/16* (2013.01); *A61M 16/0066* (2013.01); *A61M 16/04* (2013.01);
(Continued)

(58) Field of Classification Search
CPC ..... A61L 9/00; A61M 13/003; A61M 16/024; A61M 16/08; A61M 16/0833;
(Continued)

(56) References Cited

U.S. PATENT DOCUMENTS 1,727,998 A * 9/1929 Matteson ................. F24F 6/04
261/104
3,912,795 A 10/1975 Jackson
(Continued)

FOREIGN PATENT DOCUMENTS

AU    2008202098 A1    2/2009
GB       1485458 A     9/1977
(Continued)

OTHER PUBLICATIONS

International Search Report; PCT/IB2015/051830; dated Jun. 4, 2015; 3 pages.

*Primary Examiner* — Annette Dixon
(74) *Attorney, Agent, or Firm* — Knobbe, Martens, Olson & Bear, LLP

(57) ABSTRACT

A gas humidification system can have a conduit defining a gas passageway. A mass of a first absorbent material can be located in the conduit. A mass of a second absorbent material can cover at least a part of the surface of the conduit. An orifice can be located on the conduit to allow communication between the first and second absorbent materials. A heating element can be placed within, on, around, or near the first absorbent material. The heating element can heat up moisture in or on the first absorbent material such that the moisture is encouraged to join gases passing through the gas humidification system.

19 Claims, 7 Drawing Sheets

(51) Int. Cl.
*A61M 16/14* (2006.01)
*A61M 16/00* (2006.01)
*A61M 16/04* (2006.01)
*A61M 16/06* (2006.01)

(52) U.S. Cl.
CPC ...... *A61M 16/0666* (2013.01); *A61M 16/109* (2014.02); *A61M 16/1095* (2014.02); *A61M 16/142* (2014.02); *A61M 16/161* (2014.02); *A61M 2016/003* (2013.01); *A61M 2016/0027* (2013.01); *A61M 2016/103* (2013.01); *A61M 2016/1025* (2013.01); *A61M 2205/02* (2013.01); *A61M 2205/0205* (2013.01); *A61M 2205/3334* (2013.01); *A61M 2205/3368* (2013.01); *A61M 2205/3653* (2013.01); *A61M 2205/42* (2013.01); *A61M 2205/505* (2013.01); *A61M 2205/8206* (2013.01)

(58) Field of Classification Search
CPC ............ A61M 16/085; A61M 16/1045; A61M 16/1075; A61M 16/108; A61M 16/1085; A61M 16/109; A61M 16/1095; A61M 16/142; A61M 16/145; A61M 16/16; A61M 16/161; A61M 16/162; A61M 2016/0024; A61M 2016/0027; A61M 2016/0036; A61M 2205/3368; A61M 2205/3633; A61M 2205/3653; A61M 2205/3686; A61M 2205/50; A61M 2205/702; F04C 2270/041; H05B 2203/021; H05B 2203/022; H05B 3/42
See application file for complete search history.

(56) References Cited

U.S. PATENT DOCUMENTS

| | | | |
|---|---|---|---|
| 3,954,920 A | 5/1976 | Heath | |
| 4,225,542 A * | 9/1980 | Wall | A61M 16/1075 128/203.12 |
| 4,618,462 A | 10/1986 | Fisher | |
| 4,657,713 A | 4/1987 | Miller | |
| 4,676,237 A | 6/1987 | Wood et al. | |
| 5,034,162 A | 7/1991 | Chiu | |
| 5,062,145 A | 10/1991 | Zwaan et al. | |
| 5,143,655 A | 9/1992 | Chiu et al. | |
| 5,367,604 A | 11/1994 | Murray | |
| 5,611,967 A | 3/1997 | Jane et al. | |
| 5,769,071 A * | 6/1998 | Turnbull | A61M 16/16 128/203.12 |
| 5,916,493 A * | 6/1999 | Miller | A61M 16/1075 128/204.13 |
| 5,943,473 A | 8/1999 | Levine | |
| 6,010,118 A * | 1/2000 | Milewicz | A61M 13/003 261/142 |
| 6,431,118 B1 | 8/2002 | Woltmann | |
| 6,550,476 B1 * | 4/2003 | Ryder | A61M 16/1045 128/201.13 |
| 7,428,902 B2 * | 9/2008 | Du | A61M 16/1045 128/200.24 |
| 8,459,259 B2 | 6/2013 | Klasek et al. | |
| 8,550,075 B2 | 10/2013 | Virr | |
| 8,739,780 B2 | 6/2014 | Tang et al. | |
| 10,307,559 B2 * | 6/2019 | Foote | A61M 16/1075 |
| 2002/0039487 A1 | 4/2002 | Wang | |
| 2006/0012057 A1 * | 1/2006 | Anthony | A61M 16/075 261/154 |
| 2009/0044810 A1 * | 2/2009 | Kwok | A61M 16/06 128/206.28 |
| 2009/0126735 A1 | 5/2009 | Nitta | |
| 2010/0083965 A1 | 4/2010 | Virr et al. | |
| 2012/0012108 A1 | 1/2012 | Sata et al. | |
| 2012/0017905 A1 | 1/2012 | Sata et al. | |
| 2013/0239966 A1 | 9/2013 | Klasek et al. | |
| 2013/0303977 A1 | 11/2013 | Spearman et al. | |
| 2014/0001658 A1 | 1/2014 | Virr | |
| 2014/0311489 A1 | 10/2014 | Heine et al. | |
| 2015/0165146 A1 | 6/2015 | Bowman et al. | |
| 2015/0290416 A1 | 10/2015 | Klasek | |

FOREIGN PATENT DOCUMENTS

| | | | | |
|---|---|---|---|---|
| WO | WO-2005050026 A1 * | 6/2005 | ........... | F04D 29/705 |
| WO | WO 2008/095245 | 8/2008 | | |
| WO | WO 2008/095245 A1 | 8/2008 | | |
| WO | WO 2012/080941 | 6/2012 | | |
| WO | WO 2012/100291 A1 | 8/2012 | | |
| WO | WO 2015/135040 | 9/2015 | | |
| WO | WO 2015/168340 | 11/2015 | | |

* cited by examiner

HUMIDIFICATION SYSTEM

INCORPORATION BY REFERENCE TO ANY PRIORITY APPLICATIONS

Any and all applications for which a foreign or domestic priority claim is identified in the Application Data Sheet as filed with the present application are hereby incorporated by reference under 37 CFR 1.57.

TECHNICAL FIELD

The present disclosure generally relates to humidification devices. In some configurations, the present disclosure relates to humidification devices for use with respiratory therapy devices.

BACKGROUND ART

Respiratory disorders deal with the inability of a sufferer to effect a sufficient exchange of gases with the environment, leading to an imbalance of gases in the sufferer. These disorders can arise as a pathological consequence of an obstruction of the airway, insufficiency of the lungs in generating negative pressure, an irregularity in the nervous function of the brain stem, or some other physiological complication. Treatment of such disorders is diverse and depends on the particular respiratory disorder being targeted. In the first instance, a constriction of the airway, otherwise known as an obstructive apnea or a hypopnea (collectively referred to as obstructive sleep apnea or OSA), can occur when the muscles that normally keep the airway open in a patient relax during slumber to the extent that the airway is constrained or completely closed off, a phenomenon often manifesting itself in the form of snoring. When this occurs for a significant period of time, the patient's brain typically recognizes the threat of hypoxia and partially wakes the patient in order to open the airway so that normal breathing may resume. The patient may be unaware of these occurrences, which may occur as many as several hundred times per session of sleep. This partial awakening may significantly reduce the quality of the patient's sleep, over time potentially leading to a variety of symptoms, including chronic fatigue, elevated heart rate, elevated blood pressure, weight gain, headaches, irritability, depression and anxiety.

Obstructive sleep apnea is commonly treated with the application of positive airway pressure (PAP) therapy. PAP therapy involves delivering a flow of gas to a patient at a therapeutic pressure above atmospheric pressure that may reduce the frequency and/or duration of apneas, hypopneas, and/or flow limitations. This therapy may be delivered by using a positive airway pressure device (PAP device) to propel a pressurized stream of air through a conduit to a patient through an interface or mask located on the face of the patient. The stream of air may be heated to near body temperature. The stream of air may be humidified. The humidification may be performed by forcing the stream of air to travel through a respiratory humidifier containing water and a heater for heating the water. In such a system, the heater encourages the evaporation of the water, which in turn partially or fully imbues the stream of air with moisture and/or heat. This moisture and/or heat may help to ameliorate discomfort that may arise from the use of unhumidified PAP therapy.

SUMMARY

A respiratory humidifier may comprise a humidification compartment configured to hold a reservoir, and a reservoir comprising a gas inlet and a gas outlet. The reservoir in use holds a liquid, such as water or some other humidification agent (hereinafter referred to as water). The humidification compartment may comprise a resistive metallic heating plate that is connected to a source of electrical power. The resistive metallic heating plate may be configured such that it accommodates the reservoir. The reservoir may comprise a thermally conductive element to thermally link the resistive metallic heating plate with the water in the reservoir. In use, the metallic heating plate may heat up upon the application of electrical energy and transfer thermal energy to the reservoir through the thermally conductive element. The thermal energy may then assist in the heating and evaporation of the water in the reservoir such that water vapor is generated. The water vapor may join the gas stream passing through the reservoir such that gases leaving the reservoir through the gas outlet may comprise a level of moisture that is greater the level of moisture of gases entering the reservoir through the gas inlet.

As mentioned above, it is useful to provide heated and/or humidified gases to a patient being treated with gas therapies. The respiratory humidifier mentioned above may be used in conjunction with a gas source to provide heated and/or humidified gases to a patient. However, there may be difficulties in using the above-described respiratory humidifier. To carry enough water to humidify gas for a patient during the entire course of a therapy session, the reservoir used for such a respiratory humidifier must be relatively large. Because the metallic heating plate must heat the water in the entire reservoir before an acceptable level of moisture is added to gases passing through the respiratory humidifier, it may take an inconveniently long time for the temperature of the water to rise to a level acceptable for promoting the adequate humidification of gases passing through the respiratory humidifier. Additionally, if the reservoir contains water, and the respiratory humidifier is moved around or turned upside down, water may spill out from the respiratory humidifier, which may create a mess. Spills may be especially inconvenient if the humidifier is placed under, for example, the bed sheets of a patient, since the spilled water may awaken the patient or otherwise disturb the patient's sleep. Accordingly, it is an object of certain embodiments disclosed herein to provide an improved humidification system that might solve one or more of the above problems, or at least provide the public with a useful choice.

Thus, in accordance with at least one of the embodiments disclosed herein, a gas humidification system comprises a conduit defining a gas passageway, a mass of an absorbent material located within the conduit, and a heating element at least in part constructed from a positive temperature coefficient-type material, wherein the heating element is located within, on, or around the absorbent material.

In some configurations, the gas humidification system further comprises a reservoir, wherein a wall of the conduit comprises an orifice, the orifice allowing communication between the gas passageway and the reservoir.

In some configurations, the mass of absorbent material extends through the orifice at least partially into the reservoir.

In some configurations, the mass of absorbent material contacts a perimeter of the orifice.

In some configurations, the mass of absorbent material substantially blocks the orifice or reduces pneumatic communication between the gas passageway and the reservoir.

In some configurations, the mass of absorbent material comprises a wall extending at least partially along an outer surface of the absorbent material, the wall formed from a material that is less absorbent than absorbent material.

In some configurations, the wall of the absorbent material is a flexible material.

In some configurations, the wall of the conduit comprises a plurality of orifices allowing communication between the absorbent material and the reservoir.

In some configurations, the absorbent material is a hydrophilic material.

In some configurations, the conduit is formed in at least two sections, wherein the two sections are removably attached to one another or joined through a hinge to allow access to the mass of absorbent material.

In some configurations, the gas humidification system further comprises a housing, wherein at least a part of the conduit is covered by the housing, the housing forming a reservoir, and wherein a wall of the conduit comprises an orifice, the orifice allowing communication between the gas passageway and the reservoir.

In some configurations, at least part of the housing is integrally formed with the conduit.

In some configurations, the housing comprises a lid removably attached or hinged to the housing to allow access to the reservoir.

In some configurations, the housing surrounds the conduit to form an annular elongate reservoir around the conduit.

In some configurations, the gas humidification system further comprises a gases inlet and a gases outlet, and the conduit defines the gas passageway between the gases inlet and the gases outlet.

In some configurations, the mass of absorbent material is at least partially imbued with moisture.

In some configurations, the heating element interfaces with an electrical lead.

In some configurations, the electrical lead extends along a wall of the conduit.

In accordance with at least one of the embodiments disclosed herein, a gas humidification system comprises a humidifier inlet and a humidifier outlet and a gas passageway between the humidifier inlet and the humidifier outlet, a reservoir, a mass of a first absorbent material located within the gas passageway, and a mass of a second absorbent material located in the reservoir and in fluid communication with the first absorbent material.

In some configurations, the gas humidification system comprises a heating element located within, on, or around the first absorbent material.

In some configurations, the reservoir forms at least a portion of the gas passageway, in use gases passing through the reservoir, the mass of first absorbent material located inside the reservoir.

In some configurations the gas humidification system comprises a conduit defining the gas passageway separate from the reservoir, wherein a wall of the conduit comprises an orifice allowing communication between the first absorbent material and the second absorbent material.

In some configurations, the mass of first absorbent material extends through the orifice at least partially into the reservoir.

In some configurations, the mass of first absorbent material contacts a perimeter of the orifice.

In some configurations, the mass of first absorbent material substantially blocks the orifice or reduces pneumatic communication between the gas passageway and the reservoir.

In some configurations, the mass of second absorbent material holds at least a part of a volume of water stored in the in the reservoir.

In some configurations, the mass of first absorbent material comprises a wall extending at least partially along an outer surface of the first absorbent material, the wall formed from a material that is less absorbent than first absorbent material.

In some configurations, the wall of the first absorbent material is a flexible material.

In some configurations, the wall of the conduit comprises a plurality of orifices allowing communication between the first absorbent material and the second absorbent material.

In some configurations, the mass of first absorbent material comprises roots or tendrils that protrude into the mass of second absorbent material.

In some configurations, the first and/or second absorbent materials are hydrophilic materials.

In some configurations, the first absorbent material and the second absorbent material are the same material.

In some configurations, the first absorbent material and the second absorbent material are integrally formed.

In some configurations, the second absorbent material has an intrinsically higher In some configurations, the first absorbent material has an intrinsically higher moisture motility than the second absorbent material.

In some configurations, the heating element is a resistive heating element.

In some configurations, the resistive heating element is a positive temperature coefficient heating element.

In some configurations, the heating element interfaces with an electrical lead.

In some configurations, the electrical lead extends along a wall of the conduit.

In some configurations, the conduit is formed in at least two sections, wherein the two sections are removably attached to one another or joined through a hinge to allow access to the mass of first absorbent material and/or to the mass of second absorbent material.

In some configurations, at least a part of the second absorbent material is covered by a housing.

In some configurations, at least a part of the conduit is covered by the housing.

In some configurations, at least part of the housing is integrally formed with the conduit.

In some configurations, the housing comprises a lid removably attached or hinged to the housing to allow access to the second absorbent material.

In some configurations, the housing provides the reservoir.

In some configurations, the mass of second material is an annular elongate member to fit a corresponding recess formed between the housing and the conduit.

In some configurations, the mass of second absorbent material covers at least a part of an outer surface of the conduit.

In some configurations, the gas humidification system comprises a gases inlet and a gases outlet, wherein the conduit defines the gas passageway between the gases inlet and the gases outlet.

In accordance with at least one of the embodiments disclosed herein, a gas humidification system comprises a tubular conduit defining a gas passageway, a mass of an absorbent material located within the conduit, a housing at least partially covering the conduit and providing a reservoir at an outer surface of the conduit between a wall of the conduit and a wall of the housing, wherein the wall of the conduit comprises an orifice allowing communication between the absorbent material and the reservoir, and the housing having a lid for allowing access to the reservoir.

In some configurations, the housing fully circumscribes the conduit.

In some configurations, the housing is substantially tubular.

In some configurations, the housing and the conduit are concentric.

In some configurations, the gas humidification system comprises a heating element located within, on, or around the absorbent material.

In some configurations, the heating element is a resistive heating element.

In some configurations, the resistive heating element is a positive temperature coefficient heating element.

In some configurations, the heating element interfaces with an electrical lead.

In some configurations, the electrical lead extends along a wall of the conduit.

In some configurations, the mass of absorbent material extends through the orifice at least partially into the reservoir.

In some configurations, the mass of absorbent material contacts a perimeter of the orifice.

In some configurations, the mass of first absorbent material substantially blocks the orifice or reduces pneumatic communication between the gas passageway and the reservoir.

In some configurations, the mass of absorbent material comprises a wall extending at least partially along an outer surface of the absorbent material, the wall formed from a material that is less absorbent than the absorbent material.

In some configurations, the wall of the absorbent material is a flexible material.

In some configurations, the wall of the conduit comprises a plurality of orifices allowing communication between the absorbent material and the reservoir.

In some configurations, the absorbent material is a hydrophilic material.

In some configurations, the mass of absorbent material is a mass of first absorbent material and the gas humidification system further comprising a mass of second absorbent material located in the reservoir, wherein the mass of second absorbent material holds at least a part of a volume of water stored in the reservoir, the orifice allowing communication between the first absorbent material and the second absorbent material.

In some configurations, the mass of first absorbent material comprises roots or tendrils that protrude into the mass of second absorbent material.

In some configurations, the first and/or second absorbent materials are hydrophilic materials.

In some configurations, the first absorbent material and the second absorbent material are the same material.

In some configurations, the first absorbent material and the second absorbent material are integrally formed.

In some configurations, the second absorbent material has an intrinsically higher moisture capacity than the first absorbent material.

In some configurations, the first absorbent material has an intrinsically higher moisture motility than the second absorbent material.

In some configurations, the mass of second absorbent material circumscribes the conduit.

In some configurations, the housing and the conduit are concentric, and the mass of second absorbent material is an annular elongate member to fit between the housing and the conduit.

In some configurations, the conduit is formed in at least two sections, wherein the two sections are removably attached to one another or joined through a hinge to allow access to the mass of absorbent material.

In some configurations, the gas humidification system comprises a gases inlet and a gases outlet, and the conduit defines the gas passageway between the gases inlet and the gases outlet.

In accordance with at least one of the embodiments disclosed herein, a gas humidification system comprises a conduit comprising a surface, the conduit defining a gas passageway, a mass of an absorbent material covering at least a part of the surface of the conduit, and a housing integrally formed with a section of the conduit, wherein the housing at least partially covers the mass of absorbent material, and wherein the housing has a lid removably attached to the housing.

In some configurations the lid is positioned such that when the lid is removed, the absorbent material may be accessed.

In accordance with at least one of the embodiments disclosed herein, a respiratory therapy system comprises a flow generator and a gas humidification system according to any one of the above described configurations. The gas humidification system receives a flow of gases from the flow generator and increases humidity of said flow of gases. A patient interface, and a conduit to provide a flow of humidified gases from the gas humidification system to the patient interface may also be provided.

Other configurations are also described in the following. In some configurations, a gas humidification system may comprise a conduit. The conduit may comprise a surface. In some configurations, the surface may be an inner surface of the conduit. In some configurations, the surface may be an outer surface of the conduit. The conduit may define a gas passageway. Gases from a gas source may pass through the conduit on the way to an interface that pneumatically connects the airway of a patient with the gas source. The system may comprise a mass of a first absorbent material. The mass of first absorbent material may be located within the conduit. The system may comprise a mass of a second absorbent material. The mass of second absorbent material may be outside of the conduit. The second absorbent material may cover at least a part of the surface of the conduit. The conduit may comprise an orifice. The orifice may allow communication between the first absorbent material and the second absorbent material. The orifice may be located where at least a part of the surface of the conduit contacts the mass of the second absorbent material. The communication may allow for thermal communication, communication of moisture, or communication of other materials. A heating element may be located within, on, around, or near the first absorbent material. In some configurations, a heating element may be located within, on, around, or near the second absorbent material.

The first and second absorbent materials may comprise the same material. In some configurations, a singular absorbent material may be substituted for the first and second absorbent materials. The first and/or second adsorbent materials may be hydrophilic or water absorbing materials. The mass of first absorbent material and the mass of second absorbent materials may be integrally formed or be in the form of one continuous or discontinuous mass. The second absorbent material may have a higher moisture capacity than the first absorbent material. The higher moisture capacity may be due to intrinsic properties of the second absorbent material. In other words, the second absorbent material may have an intrinsically higher moisture capacity than the first absorbent material. The first absorbent material may have a higher moisture motility than the second material. In other words, the first absorbent material may allow moisture to travel through a mass of the first absorbent material at a greater velocity than if the moisture traveled through a mass of the second absorbent material. In some configurations, the first absorbent material may have an intrinsically higher moisture motility than the second absorbent material. In some configurations, the first absorbent material may have an intrinsically higher moisture capacity than the second material and/or the second absorbent material may have an intrinsically higher moisture motility than the first absorbent material. In some configurations, the first and second absorbent materials may have substantially equivalent moisture capacities and moisture motilities.

In some configurations, the heating element may be a resistive heating element. The heating element may be a positive temperature coefficient (PTC)-type heating element. In other words, the heating element may at least in part be constructed from a positive temperature coefficient-type material. In some configurations, the heating element may be entirely constructed from a positive temperature coefficient-type material. The heating element may interface with an electrical lead. The electrical lead may extend along a wall of the conduit. The second absorbent material may at least in part be covered by a housing. In some configurations, the second absorbent material may be encapsulated by the housing. In some configurations, the conduit may at least in part be covered by the housing. In some configurations, the conduit may be encapsulated by the housing. In some configurations, both the conduit and the second absorbent material may be at least in part covered or encapsulated by the housing. At least a part of the housing may be integrally formed with or be in the form of a continuous mass with at least a part of the conduit. The housing may be in multiple sections. The sections may be removably attached to one another. The sections may be attached to one another through a retention mechanism. The housing may comprise a lid. The lid may be removably attached to the housing. The housing may comprise a thread. The thread may be complementary to one or more grooves located on a surface of the lid. The lid may be positioned such that when the lid is removed, the first and/or second absorbent material may be accessed.

Additionally, in accordance with at least one of the embodiments disclosed herein, a gas humidification system is disclosed. The gas humidification system may comprise a conduit. The conduit may define a gas passageway. Gases from a gas source may pass through the conduit on the way to an interface that pneumatically connects the airway of a patient with the gas source. A mass of an absorbent material may be located within the conduit. A heating element may be present in the gas humidification system. The heating element may at least in part be constructed from a positive temperature coefficient-type material. The heating element may be within, on, around, or near the absorbent material. The mass of absorbent material may be at least partially imbued with moisture. The heating element may interface with an electrical lead or conductor that extends along a wall of the conduit.

Furthermore, in accordance with at least one of the embodiments disclosed herein, a gas humidification system is disclosed. The gas humidification system may comprise a conduit. The conduit may comprise a surface. In some configurations, the surface may be an inner surface of the conduit. In some configurations, the surface may be an outer surface of the conduit. The conduit may define a gas passageway. Gases from a gas source may pass through the conduit on the way to an interface that pneumatically connects the airway of a patient with the gas source. A mass of an absorbent material may cover at least a part of the surface of the conduit. A housing may be located on the conduit. In some configurations, the housing may be integrally formed with a section of the conduit. The housing may at least partially cover the mass of absorbent material. The housing may have a lid that is removably attachable to the housing. The lid may be positioned such that when the lid is removed, the absorbent material may be accessed.

BRIEF DESCRIPTION OF THE DRAWINGS

Specific embodiments and modifications thereof will become apparent to those skilled in the art from the detailed description herein having reference to the figures that follow, of which.

DETAILED DESCRIPTION OF SPECIFIC EMBODIMENTS

Certain features, aspects and advantages of at least one of the configurations disclosed herein include the realization that a gas humidification system can be configured such that the water used for humidification may be held within an absorbent material instead of or in addition to within a reservoir. Additionally, certain features, aspects and advantages of at least one of the configurations disclosed herein include the realization that a heater may be located within or close to the absorbent material to promote localized heating of the moisture held within the absorbent material, thereby promoting relatively rapid humidification of gases passing through the gas humidification system.

Figure 1:
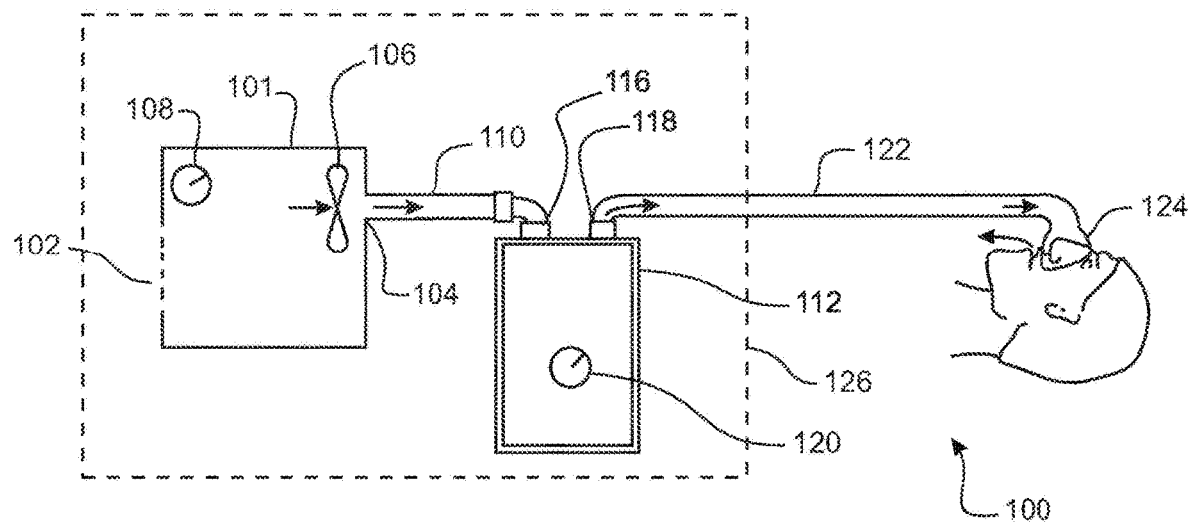
FIG. 1 shows a schematic diagram of a respiratory therapy system.

With reference to FIG. 1, a configuration for a respiratory therapy system 100 is shown. In the illustrated configuration, the respiratory therapy system 100 may comprise a flow generator 101. The flow generator 101 may comprise a gas inlet 102 and a gas outlet 104. The flow generator may comprise a blower 106. The blower 106 may comprise a motor. The motor may comprise a stator and a rotor. The rotor may comprise a shaft. An impeller may be linked to the shaft. In use, the impeller may rotate concurrently with the shaft to draw in gas from the gas inlet 102. The flow generator 101 may comprise a user interface 108, which may comprise one or more buttons, knobs, dials, switches, levers, touch screens, and/or displays so that a user might view data related to the operation of the flow generator 101 or to other components of the respiratory therapy system 100 or input operation parameters into the flow generator 101 to control its operation or the operation of other aspects of the respiratory therapy system 100. The flow generator 101 may pass gas through the gas outlet 104 to a first conduit 110. The first conduit 110 may pass the gas to a humidifier 112 that may entrain moisture in the gas to provide a humidified gas stream. The humidifier 112 may comprise a humidifier inlet 116 and a humidifier outlet 118. The humidifier 112 may comprise water or another moisturizing agent (hereinafter referred to as water). The humidifier 112 may comprise a heating element (not shown). The heating element may be used to heat the water in the humidifier 112 to encourage water vaporization and/or entrainment in the gas flow and/or increase the temperature and/or humidity of gases passing through the humidifier 112. The humidifier 112 may comprise a user interface 120 which may comprise one or more buttons, knobs, dials, switches, levers, touch screens, and/or displays so that a user might view data related to the operation of the humidifier 112 or to other components of the respiratory therapy system 100 or input operation parameters into the humidifier 112 to control the operation of the heating element, operation of other aspects of the humidifier 112, and or other aspects of the respiratory therapy system 100. Gas may then pass from the humidifier outlet 118 to a second conduit 122. The second conduit 122 may comprise a heater (not shown). The heater may be used to add heat to gases passing through the second conduit 122. The heat may reduce or eliminate the likelihood of condensation of water entrained in the gas stream along walls of the second conduit 122. The heater may comprise one or more resistive wires located in, on, or around the second conduit 122. Gas passing through the second conduit 122 may then enter a patient interface 124 that may pneumatically link the respiratory therapy system 100 to the patient's airway. The patient interface 124 may comprise a nasal mask, an oral mask, an oro-nasal mask, a full face mask, a nasal pillows mask, a nasal cannula, an endotracheal tube, a combination of the above or some other gas conveying system.

In the illustrated configuration, and as implied above, the respiratory therapy system 100 may operate as follows. Gas may be drawn into the flow generator 101 through the gas inlet 102 due to the rotation of an impeller of the motor of the blower 106. Gas may then be propelled out of the gas outlet 104 and along the first conduit 110. The gas flow may enter the humidifier 112 through the humidifier inlet 116. Once in the humidifier 112, the gas may pick up moisture. The water in the humidifier 112 may be heated by the heating element, which may aid in the humidification and/or heating of the gas passing through the humidifier 112. The gas may then leave the humidifier 112 through the humidifier outlet 118 and enter the second conduit 122. Gas may then be passed from the second conduit 122 to the patient interface 124, where it may be taken into the patient's airways to aid in the treatment of respiratory disorders.

It should be understood that the illustrated configuration should not be taken to be limiting, and that many other configurations for the respiratory therapy system 100 are possible. In some configurations, the flow generator 101 may, for example, comprise a source or container of compressed gas (e.g. air). The container may comprise a valve that may be adjusted to control the flow of gas leaving the container. In some configurations, the flow generator 101 may use such a source of compressed gas and/or another gas source in lieu of a blower 106. In some configurations the blower 106 may be used in conjunction with another gas source. In some configurations, the flow generator 101 may draw in atmospheric gases through the gas inlet 102. In some configurations, the flow generator 101 may be adapted to both draw in atmospheric gases through the gas inlet 102 and accept other gases (e.g. oxygen, nitric oxide, carbon dioxide, etc) through the same gas inlet 102 or a different inlet. In some configurations, the humidifier 112 can be integrated with the flow generator 101. In some configurations, the humidifier 112 and the flow generator 101 may share a housing 126. In some such configurations, only a single conduit extending between the flow generator 101 and the patient interface 124 need be used to convey gases to a patient. In some configurations, the flow generator 101 and the humidifier 112 may have a single user interface located on either the flow generator 101 or the humidifier 112. In some configurations, the operation of the flow generator 101, of the humidifier 112, or of other aspects of the respiratory therapy system 100 may be controlled by a controller. The controller may comprise a microprocessor. The controller may be located in or on the flow generator 101, the humidifier 112, or other parts of the respiratory therapy system 100. In some configurations, multiple controllers may be used. In some configurations, the operation of the flow generator 101, of the humidifier 112, or of other aspects of the respiratory therapy system 100 may be controlled wirelessly using a user interface located on a remote computing device. In some configurations, the respiratory therapy system 100 may comprise one or more sensors for detecting various characteristics of the gas, including pressure, flow rate, temperature, absolute humidity, relative humidity, enthalpy, oxygen concentration, and/or carbon dioxide concentration. In some configurations, there may be no user interface or a minimal user interface for the flow generator 101, humidifier 112, or other aspects of the respiratory therapy system 100. In some such configurations, the respiratory therapy system 100 may utilize a sensor to determine if the patient is attempting to use the respiratory therapy system 100 and automatically operate (e.g. the flow generator 101 may propel gases, the humidifier 112 may humidify gases, etc) according to one or more predetermined parameters if the sensor indicates that the patient is attempting to use the respiratory therapy system 100.

Figure 2A:
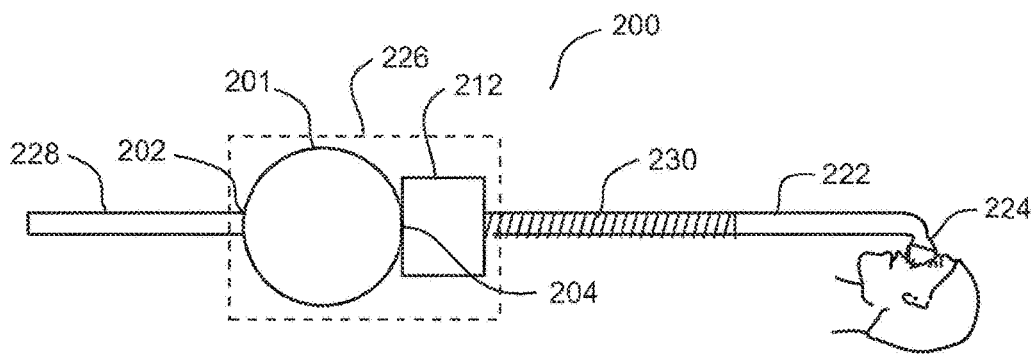
FIG. 2A shows another diagram of a respiratory therapy system.

In FIG. 2A, a similar respiratory therapy system 200 is disclosed.

Figure 2B:
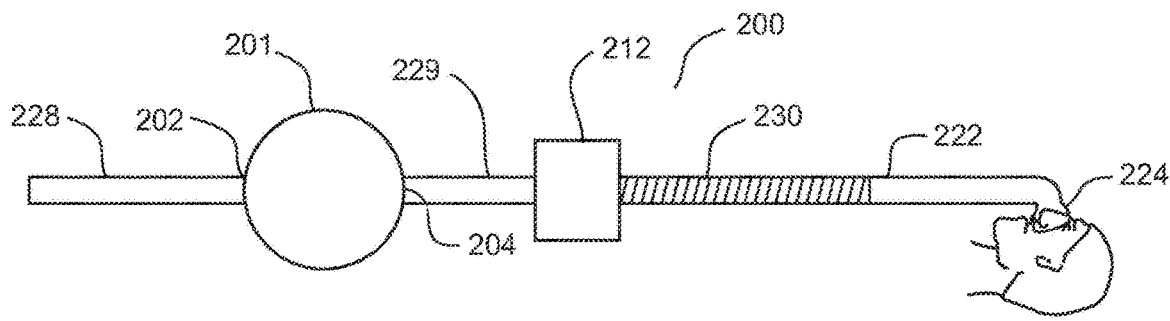
FIG. 2B shows another diagram of the respiratory therapy system of FIG. 2A.

The respiratory therapy system 200 may comprise a flow generator 201 comprising a gas inlet 202 and a gas outlet 204. The flow generator may comprise an inlet tube 228. The inlet tube 228 may be used to distance noises that may arise from the use of the gas inlet 202. The inlet tube 228 may be rigid or flexible, and may also be oriented in a variety of positions, allowing for adjustment depending on the surrounding environment. For example, if the respiratory therapy system 200 is placed on the bed of a patient, the inlet tube 228 may be oriented such that the inlet tube 228 is not obstructed by a mattress, a pillow, a bed frame, bed sheets, or other features of the environment that may be near the inlet tube 228. The respiratory therapy system 200 may comprise a gas humidification system 212. The gas humidification system 212 may be removably attached to the flow generator 201 and/or other parts of the respiratory therapy system 200. In some configurations, and as seen in FIG. 2B, a tube or tubing 229 may pneumatically link the gas humidification system 212 with the flow generator 201. The tubing 229 may be rigid or flexible. In some configurations, the flow generator 201 and the gas humidification system 212 may share a housing 226. In some such configurations, the housing 226 may be segmented such that the gas humidification system 212 may be detached from the flow generator 201. In some such configurations, the housing 226 may substantially appear to seamlessly cover both the flow generator 201 and the gas humidification system 212, but also may be separable such that the flow generator 201 and the gas humidification system 212 may be detachable. The respiratory therapy system 200 may be a modular system. In some configurations, the flow generator 201 may interface with the gas humidification system 212 and the gas humidification system 212 may be pneumatically linked with an interface 224 (for example, a mask) through an interface conduit 222. In some configurations, however, the gas humidification system 212 may be removed and the interface conduit 222 may pneumatically link the flow generator 201 and the interface 224. In some such configurations, a heat and moisture exchange (HME) device may be located in-line between the flow generator 201 and the interface 224. The interface 224 may comprise one or more apertures open to the atmosphere. The interface 224 may comprise or be linked to a valve system comprising a port that may be configured to be open to the atmosphere if the flow generator 201 is propelling gas through the respiratory therapy system 200 at or above a given flow rate or pressure and to be closed to the atmosphere if the flow generator 201 is not propelling gas through the respiratory therapy system 200 at or above a given flow rate or pressure. The conduit interface 222 may comprise a heater 230 that may heat gases passing through the interface conduit 222. The heat may prevent the condensation of moisture entrained in the gas stream along the walls of the conduit interface 222.

Figure 3A:
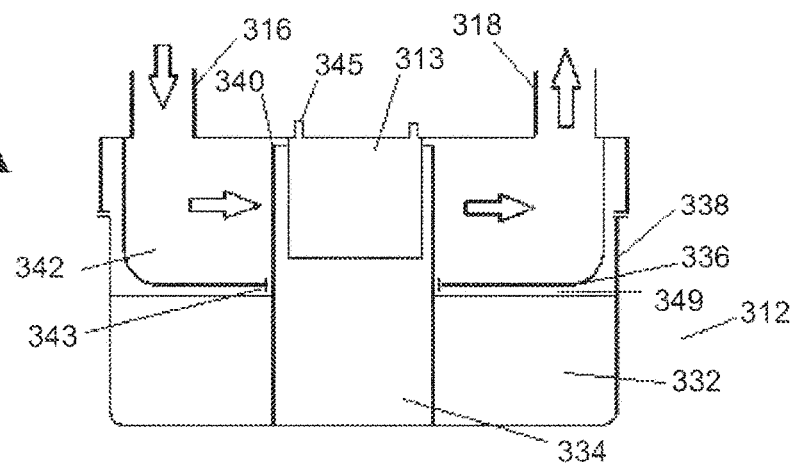
FIG. 3A shows a front view of a gas humidification system.
Figure 3B:
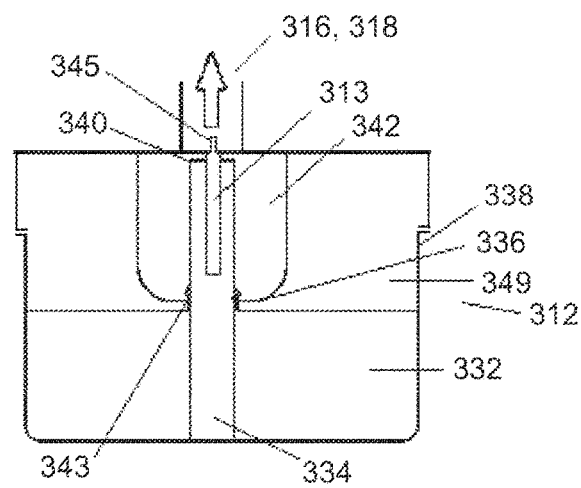
FIG. 3B shows a side view of the gas humidification system of FIG. 3A.

With reference to FIGS. 3A and 3B, front and side views, respectively, of a gas humidification system 312 are shown. The gas humidification system 312 may comprise a housing 338. The gas humidification system 312 may comprise a humidifier inlet 316 and a humidifier outlet 318. A gas passageway 342 may be present between the humidifier inlet 316 and the humidifier outlet 318. The gas passageway 342 may define a pathway that gases may follow when moving from the humidifier inlet 316 to the humidifier outlet 318. A barrier 336 may isolate the gas passageway 342 from the rest of the gas humidification system 312. The gas passageway 342 may be defined by a conduit. The barrier 336 may form a wall of the conduit. The gas humidification system 312 may comprise a reservoir 349. The housing 338 may form the reservoir 349. The reservoir 349 may be located at or near a side of the barrier 336 not in communication with the gas passageway 342. The barrier 336 or wall of the conduit may fluidly separate the gas passageway 342 from the reservoir 349. The reservoir 349 in use may comprise water 332 or some other humidification agent (hereinafter referred to as water). An orifice 343 may be present in the barrier 336 or wall to allow communication between the gas passageway 342 and the reservoir 349. In some configurations the gas passageway 342 and the reservoir 349 may be in fluid communication only via the orifice 343 in the wall of the conduit. A mass of absorbent material 334 may be present in the orifice 343. The mass of absorbent material 334 may comprise a hydrophilic material. The mass of absorbent material 334 may comprise natural or artificial sponge, melamine foam, cotton felt, textile felts or fibers, sodium polyacrylates, calcium chloride, or other materials exhibiting a relatively high capacity for retaining moisture. The mass of absorbent material 334 may comprise anti-pathogenic materials or additives such as silver or zinc-based substances. The mass of absorbent material 334 may extend at least partially into the reservoir 349. In some configurations, the mass 334 may extend at least partially into the gas passageway 342. The mass of absorbent material 334 may comprise a wall 340 that may at least partially extend along a surface of the mass of absorbent material 334. For example the wall 340 may be a coating applied to the mass of absorbent material 334. The wall 340 may be a rigid material or a flexible material. The wall 340 may be less absorbent than the absorbent material of the mass of absorbent material 334. The wall 340 may contact the walls of the opening of the barrier 336 that define the orifice 343. The contact may help to block the orifice 343 or reduce pneumatic communication between the gas passageway 342 and the reservoir 349. In some configurations the wall 340 is flexible so that the wall 340 forms a seal with the perimeter of the orifice 343. The mass of absorbent material 334 may be supported or fixed (for example, via an adhesive or mechanical fastening arrangement) along a side or wall of the gas humidification system 312 and/or of the housing 338. The mass of absorbent material 334 may be removable from the gas humidification system 312. For example, the gas humidification system 312 may be segmented in such a way that the gas humidification system 312 may comprise first and second sections that may be detached from one another or moved relative to one another to allow access to the mass of absorbent material 334 and/or other components of the gas humidification system 312. A heating element 313 may be placed in, on, around, or near the mass of absorbent material 334. Preferably, the heating element 313 is placed within the mass of absorbent material 334. Preferably the mass of absorbent material 334 tolerates high temperatures. Preferably, the mass of absorbent material 334 may protrude into the gas passageway 342 and the heating element 313 may be held within a section of the mass of absorbent material 334 that protrudes into the gas passageway 342. The heating element 313 may be electrically resistive and/or thermally conductive. The heating element 313 may comprise or interface with an electrical connection 345. The electrical connection 345 may comprise one or more electrical leads or conductors. One or more of the leads may interface with a mains power supply or may extend from a battery that may be part of or remote from the gas humidification system 312. One or more of the leads may come from a part of a respiratory therapy system (e.g. a flow generator of a respiratory therapy system) that may be used with the gas humidification system 312. The one or more leads may come from the humidifier inlet 316 and/or humidifier outlet 318, and may extend along the walls and/or housing of the gas humidification system 312 and/or along the walls of a conduit interfacing with the gas humidification system 312. In some configurations, the heating element 313 may receive power wirelessly, e.g. by resonant inductive coupling. The wireless power may be transmitted through inductive electrical power transfer technology, e.g. technologies similar to that used for the Qi interface standard for charging mobile devices. In some configurations, the heating element 313 may be constructed at least in part from a positive temperature coefficient (PTC)-type material. PTC-type materials may include ceramics (e.g. oxalates or carbonates), metals (e.g. copper or aluminum), or other materials exhibiting an increase in electrical resistivity in response to an increase in temperature. Preferably, a PTC-type material may be utilized that exhibits large increases in resistivity if the material is heated to a temperature higher than a threshold temperature. Such a PTC heating element may be called a switching type PTC heating element. A switching type PTC heater may have a substantially constant resistance (for example a small negative or positive temperature coefficient) until the heater reaches a critical temperature. As the critical temperature is approached, the heater begins to exhibit a rising positive temperature coefficient of resistance and a large increase in resistance. The resistance change may be as much as several orders of magnitude within a temperature range of a few degrees Celsius. In the illustrated configurations, the critical temperature may be in the range of about 130 degrees Celsius to about 190 degrees Celsius. The increase in resistivity may be such that the maximum temperature of the material may be limited to a particular temperature under normal operating conditions. Thus, if a PTC-type material is used, the temperature of the heating element 313 may be self-regulating. If such a PTC-type material is used for the heating element 313, the potential for the mass of absorbent material 334 to be damaged or worn by the heat emitted from the heating element 313 can be reduced. Additionally, the safety of the gas humidification system 312 can be improved.

As implied above, in some configurations the gas humidification system 312 may operate as follows. Gases may enter the gas humidification system 312 through the humidifier inlet 316. Gases may then pass through the gas passageway 342 and along the mass of absorbent material 334. Water 332 in the reservoir 349 may move from areas of high moisture potential to areas of low moisture potential via diffusion or other mechanisms of passive transport. As such, the water 332 in the reservoir 349 may be absorbed by and move along the mass of absorbent material 334. Thus the mass of absorbent material 334 may be described as a wick or a wicking pad or mass, or a wicking material. The water 332 in or on the mass of absorbent material 334 may move close to the heating element 313. The heating element 313 may be energized through the electrical connection 345 or through another source of electrical energy. The electrical energy may cause the heating element to heat up. Heat from the heating element 313 may help to mobilize and/or vaporize moisture retained in or on the mass of absorbent material 334 close to the heating element 313 such that the moisture is encouraged to join the gases passing along the mass of absorbent material 334. Humidified gases may then leave the gas humidification system 312 through the humidifier outlet 318. Advantageously, if the heating element 313 is located close to the water 332 (e.g. to the water 332 in or on the mass of absorbent material 334), a localized region of the water near the heating element 313 may be heated. As such, the entire body of water need not be heated to raise the localized region of water to an acceptable temperature sufficient for providing an adequate level of humidification to gases passing through the gas humidification system 312.

In some configurations the mass of absorbent material 334 may be provided in a 'cold pass over' humidification system, whereby the mass of absorbent material 334 is not heated by a heater element. In some configurations, water 332 in the reservoir 349 may be absorbed by and move along the mass of absorbent material 334, and gases passing through the gas passageway may be humidified by passing over the moist mass located in the gas passageway without heating.

Figure 3C:
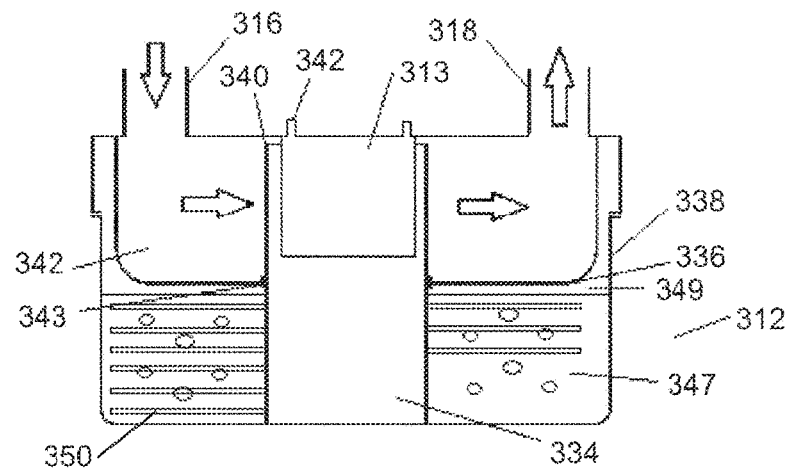
FIG. 3C shows a front view of a gas humidification system similar to that shown in FIG. 3A.

In some configurations, and as demonstrated in FIG. 3C, a mass of second absorbent material 347 may be placed in the reservoir 349. The mass of absorbent material 334 in this case may be referred to as the mass of first absorbent material or as the first mass. The second mass of second absorbent material 347 may be a hydrophilic material. Similarly, the second mass of second absorbent material 347 may comprise natural or artificial sponge, melamine foam, metal (e.g. sodium) polyacrylates, calcium chloride, or other materials exhibiting a relatively high capacity for retaining moisture. The second mass of second absorbent material 347 may be described as a wick or a wicking pad or mass, or a wicking material. The second mass of second absorbent material 347 may comprise anti-pathogenic materials or additives such as silver or zinc-based substances. In some configurations, some or all of the water 332 in the reservoir 349 not in or on the first mass may be contained in or on the second mass of second absorbent material 347. Similarly, the second mass of second absorbent material 347 may be removable from the gas humidification system 312. In some configurations, the first mass and the second mass of second absorbent material 347 may be at least in part be constructed from the same material. In some configurations, the first mass and the second mass of second absorbent material 347 may be integrally formed or be in the form of a single continuous or discontinuous mass. In some configurations, the second mass of second absorbent material 347 may comprise a material with a high capacity for retaining moisture. The second mass of second absorbent material 347 may have an intrinsically or inherently higher moisture capacity than the first mass. In some configurations, the first mass may allow moisture to move along or throughout the first mass at a higher velocity than the moisture may move along or throughout the second mass of second absorbent material 347. The velocity at which moisture may move through a material through passive transport mechanisms or other transport mechanisms may be defined as the moisture motility of the material. In some configurations, then, the first mass may intrinsically or inherently have higher moisture motility than the second mass of second absorbent material 347. The first mass and the second mass of second absorbent material 347 may interface such that water may be transferred between the first mass and the second mass of absorbent material 347. Advantageously, if a second mass of second absorbent material 347 is used to store at least a part of the water 332 in the reservoir 349, then the chance of water spills resulting from movement or rotation of the gas humidification system 312 may be reduced. In some configurations, the first mass may have tendrils or roots 350 that protrude into the second mass of second absorbent material 347. The tendrils or roots 350 can improve the moisture uptake of the first mass by allowing portions of the second mass of second absorbent material 347 distal from a core of the first mass (e.g. where the heating element 313 is located in the illustrated configurations) to more readily transfer moisture to portions of the first mass at or near the core of the first mass.

Figure 3D:
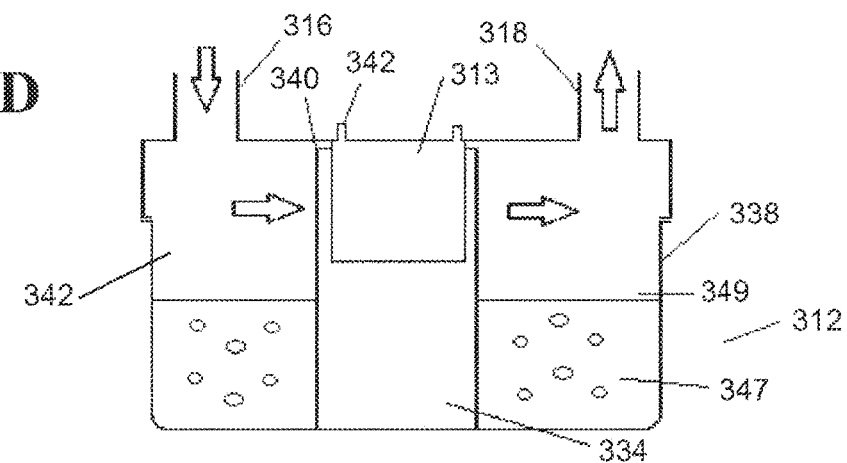
FIG. 3D shows a front view of a gas humidification system.

In some configurations the gas passageway may pass through the reservoir. In other words, in some configurations there is no barrier 336 or wall or conduit that separates the gas flow passageway from the reservoir. As illustrated in FIG. 3D, in some configurations, the reservoir 349 forms at least a portion of the gas passageway 342 so that gases pass through the reservoir 349. In some configurations the passageway 342 is provided by the reservoir 349 above an upper surface of the second mass of absorbent material 347 placed in the reservoir 349. The first mass of absorbent material may be positioned inside the reservoir 349, as shown in FIG. 3D. The gas passageway 342 through the reservoir 349 may be above an upper surface of the second mass of absorbent material 347 and/or above a water level in the reservoir 349.

Figure 4:
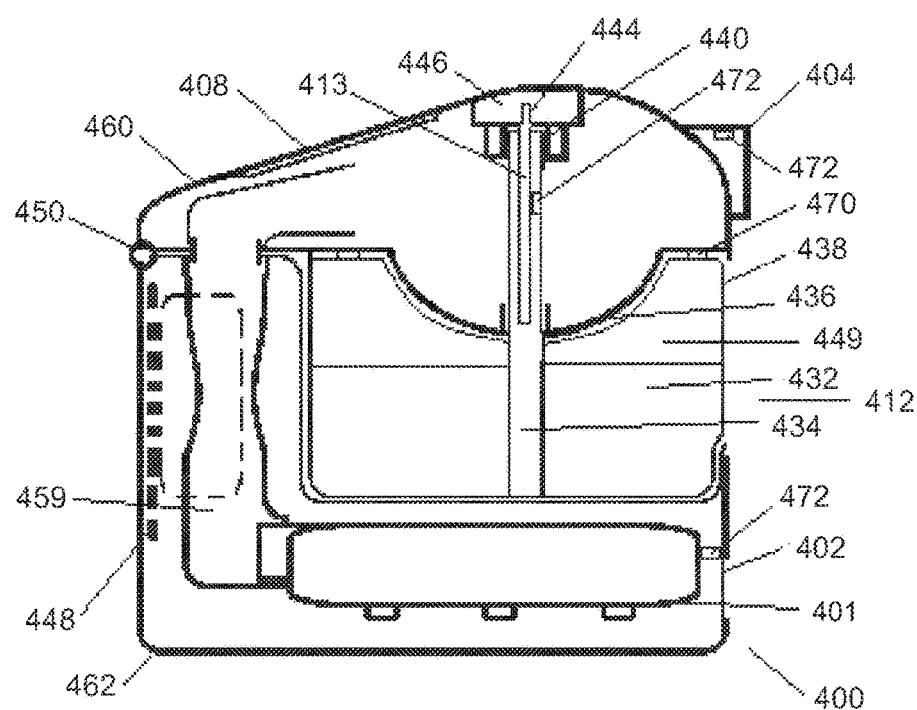
FIG. 4 shows a respiratory therapy system comprising a gas humidification system similar to those shown in FIGS. 3A-3C.

Although the gas humidification systems mentioned in the above paragraphs may be used in a variety of applications requiring moisturization of gases, similar gas humidification systems may also be used in respiratory therapy systems to moisturize respiratory gases. Many of the features of the gas humidification systems of the above paragraphs may be similarly implemented in other gas humidification systems. FIG. 4 illustrates a configuration for a respiratory therapy system 400 comprising a gas humidification system 412. The respiratory therapy system 400 may comprise a gas inlet 402 and a gas outlet 404. A flow generator 401 may be used to propel gases through the respiratory therapy system 400. The flow generator 401 may comprise a blower that may take in gases from the gas inlet 402 and propel them through the respiratory therapy system 400. The gases may pass through a flow passageway 459 and into the gas humidification system 412. As illustrated in FIG. 4, the gas humidification system 412 may be an integral part of the respiratory therapy system 400. Similarly, gases may pass along a first mass of absorbent material 434. The first mass of absorbent material 434 may for example at least partially extend into the flow passageway 459 (preferably not substantially occluding the flow passageway 459). The first mass of absorbent material 434 may at least partially extend into a reservoir 449 comprising water 432 or another humidification agent (hereinafter referred to as water). The reservoir 449 may comprise a wall 438. The first mass of absorbent material 434 may comprise a heating element 413 in or on the first mass of absorbent material 434. Similarly, the heating element 413 may comprise PTC-type material, conductive ink, wiring, or other materials configured to generate heat upon the application of energy. The heating element 413 may comprise or interface with an electrical connector 444 through which the heating element 413 may be energized with electrical energy. The electrical energy may come from an internal or external power source. The internal or external power source may transmit power directly or indirectly to a printed circuit board (PCB) 448. Many of the components of the respiratory therapy system 400, including the heating element 413, may be energized and/or controlled through the PCB 448. At least a part of the first mass of absorbent material 434 and/or heating element 413 may be held in a retaining structure 446 that may help to hold the first mass of absorbent material 434 and/or heating element 413 in place. The retaining structure 446 may be located along an interior wall of the respiratory therapy system 400. The first mass of absorbent material 434 and/or heating element 413 may be reversibly or detachably retained by the retaining structure 446. Similarly, the first mass of absorbent material 434 may comprise a flexible or rigid wall 440. The wall 440 may help to block an opening defined between the flow passageway 459 and the reservoir 449 or otherwise reduce pneumatic communication between the flow passageway 459 and the reservoir 449. In some configurations the wall 440 is flexible so that the wall 440 forms a seal with the perimeter of the opening. Additionally, a barrier 436 may be present to help separate the flow passageway 459 and the reservoir 449. Water 432 may be drawn up into and/or onto the first mass of absorbent material 434 from the reservoir 449, and may travel through and/or along the first mass of absorbent material 434 via passive transport mechanisms or other transport mechanisms such that moisture eventually comes close to or reaches the heating element 413. The heating element 413 may heat the water 432 at or near the heating element 413 such that the water is encouraged to join the gas moving along the flow passageway 459. Humidified gases may then leave the respiratory therapy system 400 through the gas outlet 404. The respiratory therapy system 400 may comprise a first section 460 and a second section 462. The first section 460 may be a lid of the respiratory therapy system 400 and the second section 462 may be a base of the respiratory therapy system 400. The sections 460, 462 may be removably attached to one another. The sections 460, 462 may be joined through a hinge 450. The hinge 450 may allow the sections 460, 462 to pivot relative to one another. In some configurations, the sections 460, 462 may be moved apart using the hinge 450 to allow access to the first mass of absorbent material 434, heating element 413, and/or other components of the respiratory therapy system 400. In some configurations, and similarly to the gas humidification system demonstrated in FIG. 3C and in the above paragraphs, a second mass of absorbent material may be used in the reservoir 449. The water 432 may be partially or fully stored within the second mass of absorbent material. In some configurations, the reservoir 449 may be removed from the respiratory therapy system 400 to allow access to the water 432, first mass of absorbent material 434 (e.g. for removal, replacement, and/or disinfection), and/or second mass of absorbent material (e.g. for removal, replacement, and/or disinfection). In some configurations, the first section 460, the second section 462, and/or the wall 438 of the reservoir 449 may comprise or interface with a sealing structure 470 that may help to pneumatically seal components of the respiratory therapy system 400. The respiratory therapy system 400 may comprise one or more sensing arrangements 472 (located at or near, for example, the gas inlet 402, the gas outlet 404, and/or the heating element 413) capable of sensing various characteristics of gases passing through the respiratory therapy system 400 or characteristics of the environment surrounding the sensing arrangement 472, including pressure, flow rate, temperature, absolute humidity, relative humidity, enthalpy, oxygen concentration, and/or carbon dioxide concentration. The sensed characteristics may be used to aid in the control of the respiratory therapy system 400, which may be controlled using, for example, an open loop controller or closed loop controller. The sensing arrangement 472 may comprise a housing that may protect the contents of the sensing arrangement 472. The respiratory therapy system 400 may also comprise a user interface 408 that may be used to control aspects of the respiratory therapy system 400.

Figure 5A:
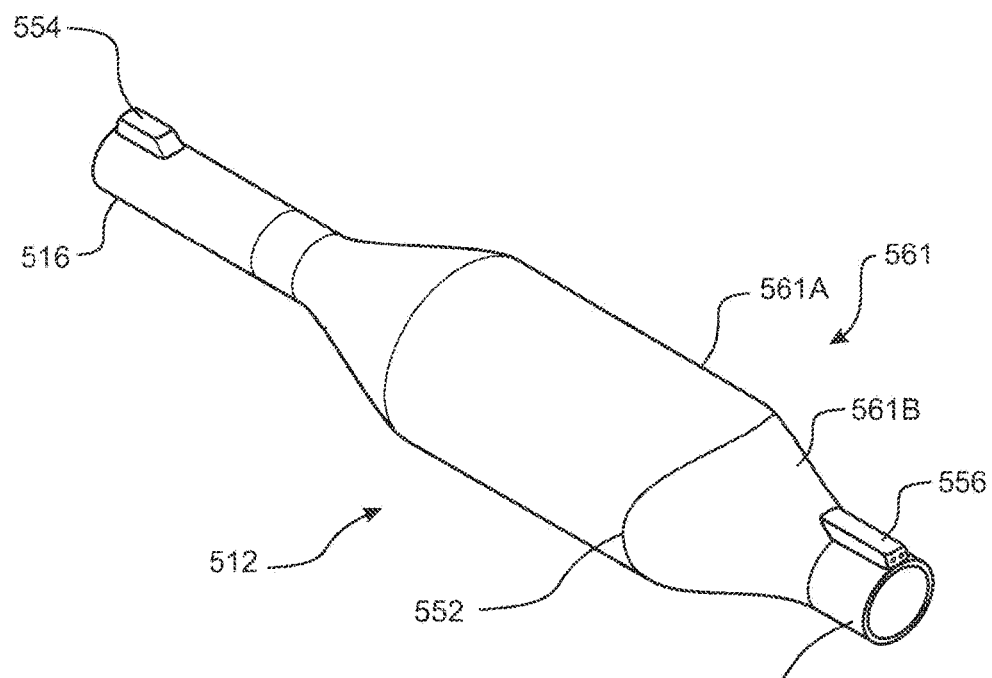
FIG. 5A shows a perspective view of a gas humidification system.

Another gas humidification system is demonstrated in FIGS. 5A-5E. FIG. 5A shows a perspective view of a gas humidification system 512. The gas humidification system 512 may comprise a conduit 563. In some configurations the conduit 563 is a tubular conduit. The conduit 563 may comprise multiple sections which may be reversibly separable. A housing 561 may at least partially cover the conduit 563. The housing 561 may come in multiple sections. For example, the housing 561 may comprise a first section or base 561A and a second section or lid 561B. Two or more of the sections may be reversibly attached and detached from one another. A detachment mechanism 552 may be used to alternately separate and join the sections of the housing 561, or to move the sections apart from one another. For example, the detachment mechanism 552 may comprise a screw thread on one section of the housing 561 and a complementary recess on another section of the housing 561, such that the sections may be assembled and dissembled with a rotary motion. In some configurations, the detachment mechanism 552 may comprise a releasable latch on one section of the housing 561 and a complementary catch on another section of the housing 561. One section of the housing 561 may be connected to another section of the housing 561 via a hinging or swiveling mechanism so as to allow the sections to pivot and/or move relative to one another. Other fasteners may be used for other configurations of the detachment mechanism 552. A seal may be located between the sections of the housing 561. The seal may help to prevent pneumatic communication or other forms of communication between the housing 561 and the other components of the gas humidification system 512. The conduit 563 may define a gas passageway. The gas humidification system 512 may comprise a humidifier inlet 516 and a humidifier outlet 518. The conduit 563 may extend from the humidifier inlet 516 to the humidifier outlet 518. The gas humidification system 512 may comprise a first electrical connector 554. The first electrical connector 554 may be located on a first side of the conduit 563 or housing 561. The first electrical connector 554 may send and/or receive electrical energy to and/or from an electrical conductor that may mate with the first electrical connector 554. The electrical conductor may come from a component of a respiratory therapy system (e.g. a flow generator or heated conduit) that may be connected to the gas humidification system 512. In some configurations, the first electrical connector 554 may be positioned on or near the humidifier inlet 516. In some such configurations, the first electrical connector 554 and the humidifier inlet 516 may couple together with a complementary gas passageway and electrical connector in or on the component of the respiratory therapy system. The combination of the first electrical connector 554 and the humidifier inlet 516 may thus form an electro-pneumatic connection with the component. The gas humidification system 512 may comprise a second electrical connector 556. Similarly, the second electrical connector 556 may send and/or receive electrical energy to and/or from an electrical conductor (e.g. a conductor of a heated conduit) that may mate with the second electrical connector 556. In some configurations, the first electrical connector 554 and/or the second electrical connector 556 may be used to send and/or receive data (for example data obtained from a sensor located in the gas humidification system 512 or another component of a respiratory therapy system connected to the gas humidification system 512.

Figure 5B:
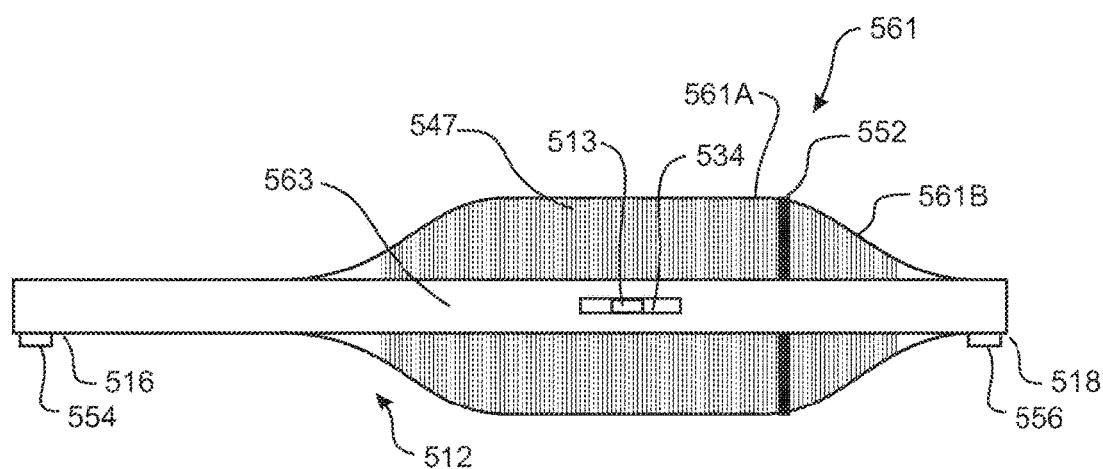
FIG. 5B shows a top-down cross-sectional view of the gas humidification system of FIG. 5A.
Figure 5C:
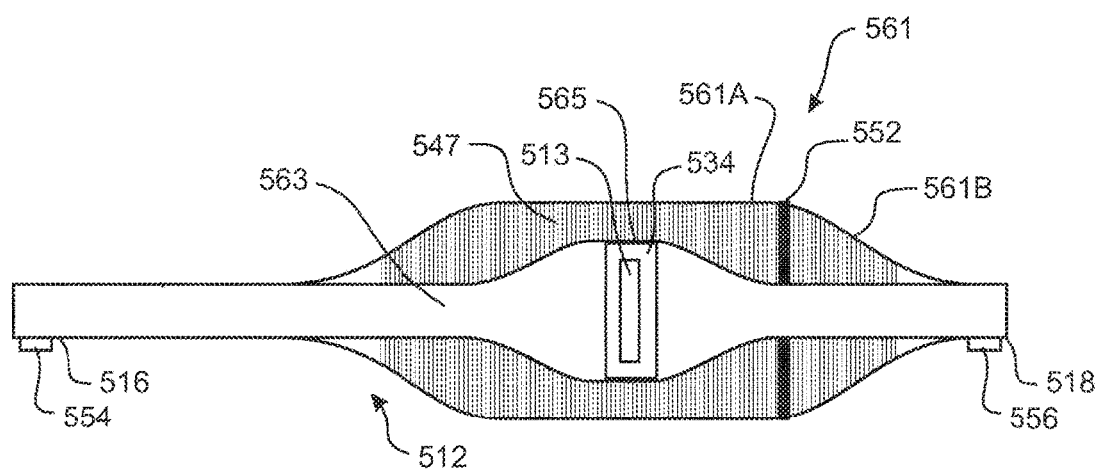
FIG. 5C shows a side cross-sectional view of the gas humidification system of FIGS. 5A and 5B.
Figure 5D:
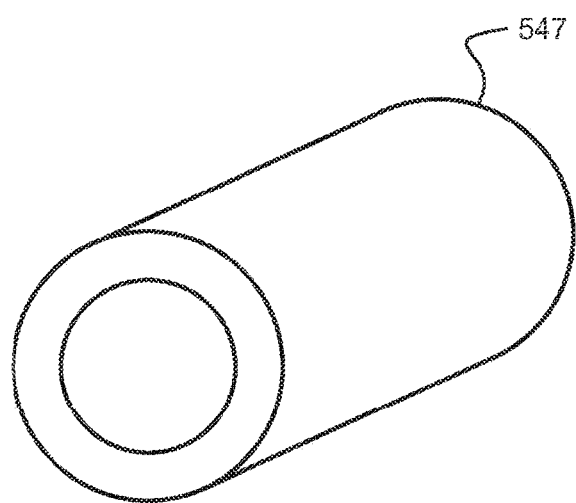
FIG. 5D shows an absorbent material.

FIGS. 5B and 5C demonstrate additional features, aspects and advantages of the gas humidification system 512. As described above, the housing 561 may comprise two sections: a first section or base 561A and a second section or lid 561B. At least a part of the housing 561 may be integrally formed with or be in the form of a continuous mass with at least a part of the conduit 563. The gas humidification system 512 may comprise a second mass of absorbent material 547. The second mass of absorbent material 547 may be located outside the conduit 563. The second mass of absorbent material 547 may be placed at least in part in the housing 561 between a surface of the conduit 563 and a wall of the housing 561. In some configurations the housing 561 provides or contains a reservoir for containing water and/or the second mass of absorbent material 547. The second mass of absorbent material 547 may be sized and shaped such that it fits within the space defined by the recess between the surface of the conduit 563 and the wall of the housing 561. For example, if the recess comprises an elongate annular shape, the second mass of absorbent material 547 may be in the form of a cylindrical sheet (an annular elongate member) as seen in FIG. 5D. In some configurations the housing 561 may fully circumscribe the conduit 563, that is, the housing 561 may extend fully around a perimeter of the conduit 563 as illustrated in FIGS. 5A to 5G. In some configurations the housing 561 is substantially tubular. In some configurations the housing 561 and the conduit 563 may be concentric so that an annular space or recess is formed by the housing 561 around the conduit 563 for receiving the second mass of absorbent material 547. The housing 561 may provide a reservoir for holding the second mass of absorbent material 547 and/or humidification fluid (for example water), and the conduit 563 may extend through the reservoir. A first mass of absorbent material 534 may be present in the conduit 563. The first mass of absorbent material 534 may comprise a heating element 513 in, on, or near the first mass of absorbent material 534. The heating element 513 may at least in part be constructed from a PTC-type material. The heating element 513 may receive electrical energy directly or indirectly through the first electrical connector 554 and/or the second electrical connector 556, or from some other energy source. One or more thermistors or other temperature measuring elements, structures or arrangements may interface with the heating element 513 to measure the temperature of the heating element 513. The measured temperature may be communicated to a controller of the gas humidification system 512 to facilitate control of the temperature of the heating element 513. One or more orifices 565 may be along the conduit 563. The orifices 565 may allow physical, fluid, and/or other forms of communication between the first mass of absorbent material 534 and the second mass of absorbent material 547. In some configurations, the first mass of absorbent material 534 may have tendrils or roots that protrude into the second mass of absorbent material 547. The tendrils or roots can improve the moisture uptake of the first mass of absorbent material 534 by allowing portions of the second mass of absorbent material 547 distal from a core of the first mass 534 (e.g. where the heating element 513 is located in the illustrated configurations) to more readily transfer moisture to portions of the first mass of absorbent material 534 at or near the core of the first mass of absorbent material 534. The first mass of absorbent material 534 and the second mass of absorbent material 547 may be separate masses, or may be integrally formed or may be a single continuous or discontinuous mass. The first mass of absorbent material 534 and the second mass of absorbent material 547 may comprise different absorbent materials or the same absorbent materials. In some configurations, the absorbent material of the second mass of absorbent material 547 may have an intrinsically higher moisture capacity than the absorbent material of the first mass of absorbent material 534. In some configurations, the absorbent material of the first mass of absorbent material 534 may have an intrinsically higher moisture motility than the absorbent material of the second mass of absorbent material 547. In some configurations, and as illustrated in FIG. 5G, one or more openings 588 may be located along the walls of the conduit 563 allowing communication between the second mass of absorbent material 547 and the gas passageway defined by the conduit 563. The openings 588 may help to muffle sounds generated by the passing of gas through the gas humidification system 512. The second mass of absorbent material 547 may help to absorb some or all of the sounds generated by the passage of the gas. In some such configurations, the second mass of absorbent material 547 may be constructed at least in part from a material that dampens acoustic vibrations caused by gases passing through the gas humidification system 512.

In use, the sections 561A, 561B of the housing 561 may be separated or moved relative to each other via the detachment mechanism 552. The second mass of absorbent material 547 may be removed from the housing 561. Once removed, the second mass of absorbent material 547 may be moistened with water or another humidification agent (hereinafter referred to as water) and returned to the housing 561. Alternatively, the sections 561A, 561B of the housing 561 may be separated and the housing may be oriented such that the open side of the housing 561 may point upwards. Water may be directly poured into the open side of the housing 561 to imbue the second mass of absorbent material 547 with water. If the second mass of absorbent material 547 is in the housing 561 and comprises water, moisture from the second mass of absorbent material 547 may be transferred to the first mass of absorbent material 534 and along or through the first mass of absorbent material 534 through the orifice 565. The water may move along the first mass of absorbent material 534 and the second mass of material 547 through passive transport mechanisms. Water at or near the heating element 513 in, on, or near the first mass of absorbent material 534 may be heated by the heating element 513. If gases are passing through the gas humidification system 512, the heated water may be encouraged to join the gases such that humidified gases may leave the gas humidification system 512.

Figure 5E:
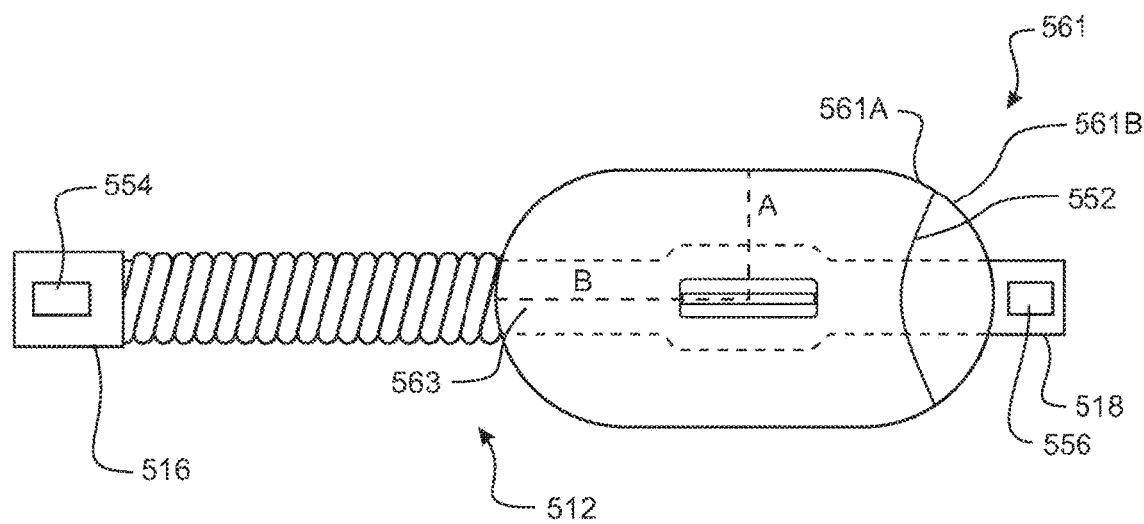
FIG. 5E shows a top-down view of a gas humidification system.
Figure 5F:
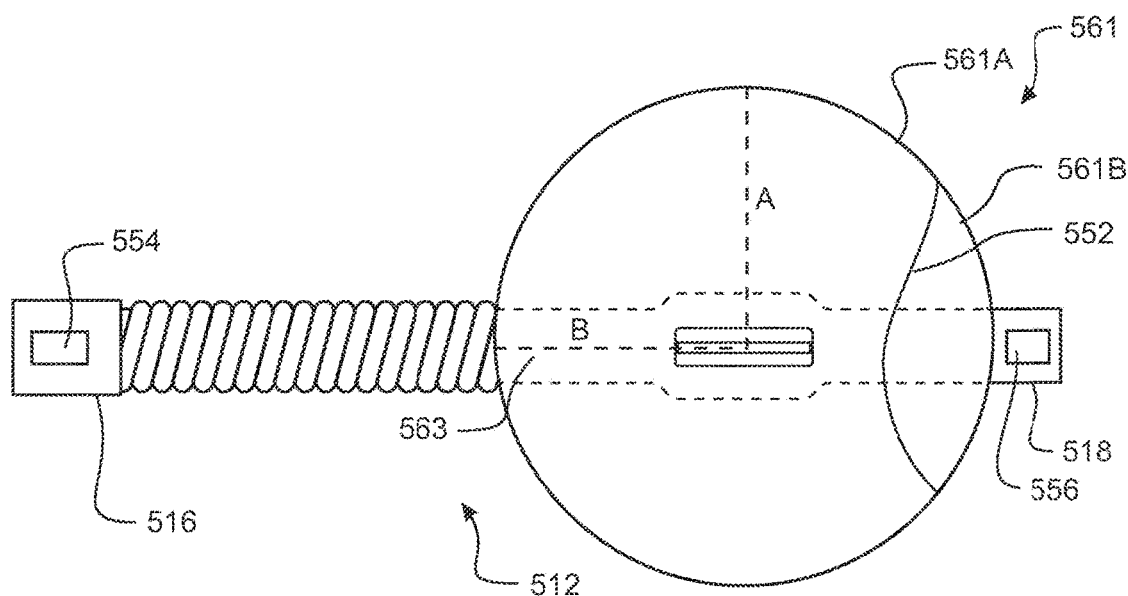
FIG. 5F shows a top-down view of a gas humidification system similar to the system shown in FIG. 5E.
Figure 5G:
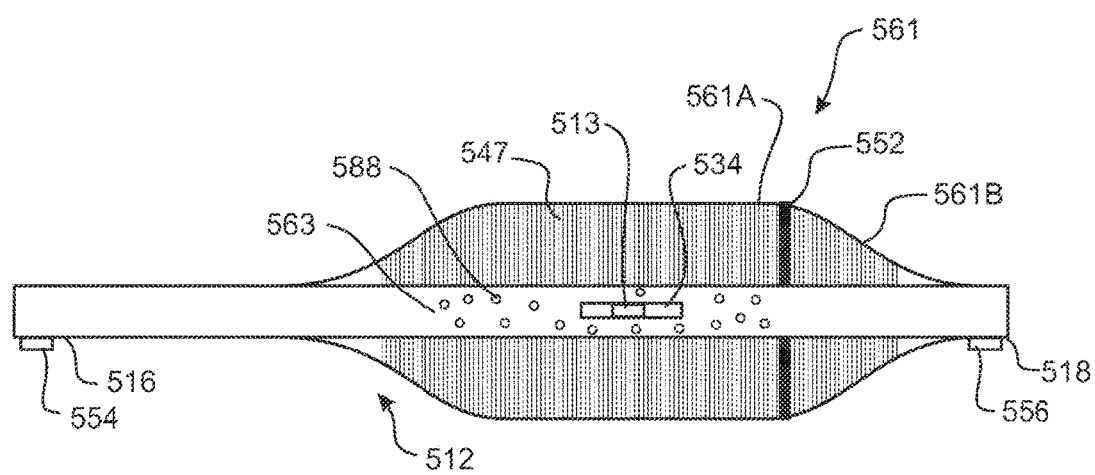
FIG. 5G shows an alternative gas humidification system similar to the system shown in FIG. 5B.

FIGS. 5E and 5F demonstrate different sizes and shapes for the housing 561 of the gas humidification system 512. Many different sizes and shapes for the housing 561 and for the second mass of absorbent material 547 may be used. FIG. 5E demonstrates an elongate roughly ellipsoidal housing wherein the radius along the B axis is substantially longer than the radius along the A axis. FIG. 5F demonstrates a roughly ellipsoidal housing wherein the radius along the B axis is relatively closer to the radius along the A axis. In some configurations, water from the second mass of absorbent material 547 may more evenly reach the first mass of absorbent material 534 and the heating element 513 if the housing 561 has an ellipsoidal shape where the radius along the A axis is close to the radius along the B axis and the second mass of absorbent material 547 is shaped and sized to match the housing 561. In other words, as the ratio of the radius along the A axis over the ratio along the B axis approaches 1, if the second mass is sized and shaped to fit substantially snugly within the confines of the housing 561, the water from the second mass of absorbent material 547 may increasingly more evenly reach the first mass of absorbent material 534. By water evenly reaching the first mass of absorbent material 534, it may be understood that water at different points in the part of the second mass of absorbent material 547 located along the walls of the housing 561 at a given point in time may have a substantially similar time of arrival to the first mass of absorbent material 534. The utilization of moisture entrained within the second mass of absorbent material 547 over the course of a therapy session may be more efficient with the gas humidification system 512 shown in FIG. 5F than with the gas humidification system 512 shown in FIG. 5E.

Unless the context clearly requires otherwise, throughout the description and the claims, the words "comprise", "comprising", and the like, are to be construed in an inclusive sense as opposed to an exclusive or exhaustive sense, that is to say, in the sense of "including, but not limited to."

Where, in the foregoing description reference has been made to integers or components having known equivalents thereof, those integers are herein incorporated as if individually set forth.

The invention may also be said broadly to consist in the parts, elements and features referred to or indicated in the specification of the application, individually or collectively, in any or all combinations of two or more of said parts, elements or features.

Reference to any prior art in this specification is not, and should not be taken as, an acknowledgement or any form of suggestion that that prior art forms part of the common general knowledge in the field of endeavour in any country in the world.

Certain features, aspects and advantages of some configurations of the present disclosure have been described with reference to use of the gas humidification system with a respiratory therapy system. However, certain features, aspects and advantages of the use of the gas humidification system as described may be advantageously be used with other therapeutic or non-therapeutic systems requiring the humidification of gases. Certain features, aspects and advantages of the methods and apparatus of the present disclosure may be equally applied to usage with other systems.

Although the present disclosure has been described in terms of certain embodiments, other embodiments apparent to those of ordinary skill in the art also are within the scope of this disclosure. Thus, various changes and modifications may be made without departing from the spirit and scope of the disclosure. For instance, various components may be repositioned as desired. Moreover, not all of the features, aspects and advantages are necessarily required to practice the present disclosure. Accordingly, the scope of the present disclosure is intended to be defined only by the claims that follow.

What is claimed is:

1. A gas humidification system comprising:
a conduit defining a gas passageway,
a mass of first absorbent material,
a heating element at least in part constructed from a positive temperature coefficient-type material,
a reservoir, and
a mass of second absorbent material,
wherein the heating element is located within, on, or around the mass of first absorbent material,
wherein a wall of the conduit comprises an orifice, the orifice allowing communication between the gas passageway and the reservoir,
wherein the mass of first absorbent material extends through the orifice, and
wherein the mass of first absorbent material and the mass of second absorbent material are in fluid communication through the orifice.

2. The gas humidification system as claimed in claim 1, wherein the mass of first absorbent material contacts a perimeter of the orifice.

3. The gas humidification system as claimed in claim 2, wherein the mass of first absorbent material substantially blocks the orifice or reduces pneumatic communication between the gas passageway and the reservoir.

4. The gas humidification system as claimed in claim 1, wherein the mass of first absorbent material comprises a wall extending at least partially along an outer surface of the mass of first absorbent material, the wall formed from a material that is less absorbent than the mass of first absorbent material.

5. The gas humidification system as claimed in claim 4, wherein the wall of the mass of first absorbent material is a flexible material.

6. The gas humidification system as claimed in claim 1 wherein the wall of the conduit comprises a plurality of orifices allowing communication between the mass of first absorbent material and the reservoir.

7. The gas humidification system as claimed in claim 1, wherein the mass of first absorbent material is a hydrophilic material.

8. The gas humidification system as claimed in claim 1, wherein the conduit is formed in at least two sections, wherein the two sections are removably attached to one another or joined through a hinge to allow access to the mass of first absorbent material.

9. The gas humidification system as claimed in claim 1, further comprising a housing, wherein at least a part of the conduit is covered by the housing, the housing forming the reservoir.

10. The gas humidification system as claimed in claim 9, wherein at least part of the housing is integrally formed with the conduit.

11. The gas humidification system as claimed in claim 10, wherein the housing comprises a lid removably attached or hinged to the housing to allow access to the reservoir.

12. The gas humidification system as claimed in claim 9, wherein the housing surrounds the conduit to form an annular elongate reservoir around the conduit.

13. The gas humidification system as claimed in claim 1, further comprising a gases inlet and a gases outlet, and the conduit defines the gas passageway between the gases inlet and the gases outlet.

14. The gas humidification system as claimed in claim 1, wherein the mass of first absorbent material is at least partially imbued with moisture.

15. The gas humidification system as claimed in claim 1, wherein the heating element interfaces with an electrical lead.

16. The gas humidification system as claimed in claim 15, wherein the electrical lead extends along a wall of the conduit.

17. The gas humidification system as claimed in claim 1, wherein the mass of first absorbent material is at least in part constructed from the same material as the mass of second absorbent material.

18. The gas humidification system as claimed in claim 1, wherein the mass of first absorbent material is located within the conduit, wherein the mass of second absorbent material is located within the reservoir.

19. The gas humidification system as claimed in claim 1, wherein the mass of first absorbent material is located within the conduit and extends through the orifice at least partially into the reservoir.

* * * * *